(12) United States Patent
Dai et al.

(10) Patent No.: US 10,114,006 B2
(45) Date of Patent: Oct. 30, 2018

(54) SELF-DIAGNOSIS METHOD AND APPARATUS FOR MEASURING RESULTS FROM BLOOD ANALYZERS

(71) Applicant: Shenzhen Mindray Bio-Medical Electronics Co., Ltd., Shenzhen (CN)

(72) Inventors: Yong Dai, Shenzhen (CN); Daxin Huang, Shenzhen (CN)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 943 days.

(21) Appl. No.: 14/355,548

(22) PCT Filed: Oct. 25, 2012

(86) PCT No.: PCT/CN2012/083483
§ 371 (c)(1),
(2) Date: Jun. 27, 2014

(87) PCT Pub. No.: WO2013/064032
PCT Pub. Date: May 10, 2013

(65) Prior Publication Data
US 2015/0177222 A1    Jun. 25, 2015

(30) Foreign Application Priority Data

Oct. 31, 2011  (CN) .......................... 2011 1 0337467

(51) Int. Cl.
*G01N 33/49* (2006.01)
*A61B 5/1455* (2006.01)
(Continued)

(52) U.S. Cl.
CPC ............ *G01N 33/49* (2013.01); *A61B 5/0059* (2013.01); *A61B 5/1455* (2013.01); *G01N 21/59* (2013.01);
(Continued)

(58) Field of Classification Search
USPC ........................................................ 702/183
See application file for complete search history.

(56) References Cited

U.S. PATENT DOCUMENTS

| | | | | |
|---|---|---|---|---|
| 5,285,782 A | * | 2/1994 | Prosser | A61B 5/14551 256/41 |
| 5,935,076 A | * | 8/1999 | Smith | A61B 3/1233 356/41 |

(Continued)

FOREIGN PATENT DOCUMENTS

| | | |
|---|---|---|
| CN | 1281146 A | 1/2001 |
| CN | 1864060 A | 11/2006 |

(Continued)

*Primary Examiner* — Paul D Lee
(74) *Attorney, Agent, or Firm* — Polsinelli LLP; Kory D. Christensen (57) ABSTRACT

A self-diagnosis method and apparatus for measuring results from blood analyzers, the method comprising: generating an acquisition transmittance curve according to the changes in transmittance rate of sample during a sample acquisition process; determining whether there is an anomaly in the acquisition process according to the acquisition transmittance rate curve; if there is no anomaly in the acquisition process, determining that the measurement results of the blood sample are credible; and if there is an anomaly in the acquisition process, determining that there is a doubt about the measured results of the blood samples, the self-diagnosis method and apparatus for measuring results from blood analyzer can improve the accuracy of self-diagnosis of measured results from blood analyzers, and reducing the false positive rate, at the same time, the workload of users in examining and verifying the measured results is reduced, thereby saving on measuring costs.

12 Claims, 6 Drawing Sheets

(51) Int. Cl.
*A61B 5/00* (2006.01)
*G01N 21/59* (2006.01)
*G01N 21/84* (2006.01)
*G01N 35/00* (2006.01)

(52) U.S. Cl.
CPC ....... *G01N 21/84* (2013.01); *G01N 35/00594* (2013.01); *G01N 2201/02* (2013.01); *G01N 2201/12* (2013.01)

(56) References Cited

U.S. PATENT DOCUMENTS

| | | | |
|---|---|---|---|
| 6,240,306 B1 * | 5/2001 | Rohrscheib | A61B 5/0059 250/341.6 |
| 2001/0009265 A1 * | 7/2001 | Schulz | A61B 5/02427 250/227.14 |
| 2002/0133255 A1 * | 9/2002 | Wardlaw | G06F 19/366 700/109 |
| 2005/0203356 A1 * | 9/2005 | Samsoondar | A61B 5/00 600/322 |
| 2013/0096836 A1 * | 4/2013 | Feldschuh | A61B 5/02755 702/19 |

FOREIGN PATENT DOCUMENTS

| | | |
|---|---|---|
| CN | 101246113 A | 8/2008 |
| CN | 101846671 A | 9/2010 |
| WO | WO99/40432 A1 | 8/1999 |
| WO | WO2010128575 A1 | 11/2010 |

* cited by examiner

| Comparison | | HGB | RBC | MCHC | Acquisition | Alarm |
|---|---|---|---|---|---|---|
| Before Using Self-Diagnostic Function | HGB Measurement Result Anomalies | 80g/L | 3.61*1012/L | 228g/L | Anomaly | No |
| | Re-Measurement Measurement Result | 117g/L | 3.66*1012/L | 320g/L | Normal | No |
| After Using Self-Diagnostic Function | HGB Measurement Result Anomaly | *** | 3.61*1012/L | *** | Anomaly | Acquisition Not Enough |
| | Re-Measurement Measurement Result | 117g/L | 3.66*1012/L | 320g/L | Normal | No |

SELF-DIAGNOSIS METHOD AND APPARATUS FOR MEASURING RESULTS FROM BLOOD ANALYZERS

TECHNICAL FIELD

This disclosure relates generally to medical devices. Particularly, this disclosure relates to self-diagnosis methods and apparatuses for measuring results from blood analyzers.

SUMMARY

Disclosed herein are embodiments of self-diagnosis method for measuring results from blood analyzers, expanders thereof and self-diagnosis apparatuses.

In one aspect, a self-diagnosis method for measurement results from a blood analyzer is provided that can include: generating an acquisition transmittance curve according to changes in transmittance of a blood sample during a sample acquisition process; determining whether there is anomaly in the acquisition process according to acquisition transmittance curve; if there is no anomaly in the acquisition process, determining that the measured results of the blood sample are credible; if there is anomaly in the acquisition process, determining that there is a doubt about the measurement results of the blood sample.

In another aspect, providing a self-diagnosis apparatus for measurement results from a blood analyzer, comprising: an acquisition monitoring module, generating an acquisition transmittance curve according to changes in transmittance of a blood sample during an acquisition process, and determining whether there is an anomaly in the acquisition process according to the acquisition transmittance curve; the first determination module, determining whether the measurement results of the blood sample are credible according to whether there is an anormaly in the acquisition process; if there is no anomaly in the acquisition process, determining that the measured results are credible; if there is an anomaly in the acquisition process, determining that there is a doubt about the measurement results.

The self-diagnosis methods and apparatuses for measuring results from blood analyzers described herein, by real-time monitoring of the acquisition transmittance curve during a sample acquisition process, can determine whether there is an anomaly in the acquisition process according to the acquisition transmittance curve, and whether the measurement results of blood samples are credible using clinical statistics, thereby improving the accuracy of self-diagnosis of measured results from blood analyzers, and reducing the false positive rate. The self-diagnosis methods and apparatuses may also reduce the workload of users in examining and verifying the measured results, thereby saving on measurement costs.

DETAILED DESCRIPTION

Blood analyzers are widely used in hospitals, and the parameters of the blood analyzers are often divided into three kinds: leukon, erythroid (erythrocyte and hemoglobin) and platelets. These three kinds may also be divided into dozens of parameters, and the more advanced the blood analyzer, the more parameters it can measure.

In big hospitals, a large number of blood samples are measured by blood analyzers every day. Whether there are any anomalies in the measurement results, and what may lead to the anomalies (blood samples or blood analyzers) all need to be determined by the doctors.

Statistical results show that 70% of anomalies in the measurement results of normal persons are caused by blood samples preparation or acquisition, so sample acquisition is one of the main reasons which causes anomalies in measurement results.

To solve the problem that anomalies in measurement results are mainly caused by sample acquisition, and to improve the ability to identify anomalies in measurement results and blood analyzers, two types of methods are often used: (1) Improving sensitivity of clinical alarms of the blood analyzers, and automatically identifying the anomalies in measurement results in view of clinical statistics, (2) monitoring the work status of the blood analyzers, if the anormal status is found frequently during measurements, the analyzers will alarm and shield all of the measurement results during such anormal status.

The methods mentioned above may improve the ability to identify the anomalies in measurement results and the anomaly status for blood analyzers, thereby reducing the pressure on the doctors to check the results, but there can be some shortcomings associated with such methods. As to method (1), the anomalies in the measurement results can only be identified in view of clinical statistics, but the reason(s) behind such anormal results may not be identified. In this case, the probability of false positive reports (i.e., the blood samples is not anormal in fact, but be determined as anormaly) can be relatively high, and the cost may be increased by unnecessary re-measurements. As to method (2), the anormal status of the blood analyzers during measurements may not necessarily cause the anomalies in the measurement results. So the probability of false positive reports can also be relatively high, and the process of continuous measurements may often be interrupted.

A detailed description of methods and apparatuses in accordance with embodiments of the present disclosure is provided below. While several embodiments are described, it should be understood that this disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

Figure 1:
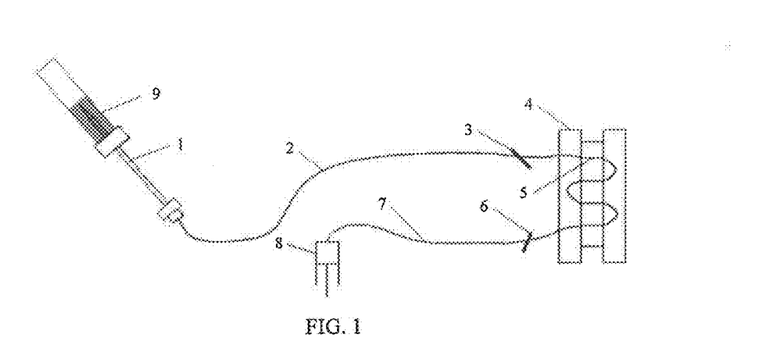
FIG. 1 shows a schematic diagram of an acquisition subsystem of a blood analyzer using a blood sample injecting valve.

The structure and work flow of an example blood analyzer is first introduced below. FIG. 1 shows a schematic diagram of a sample acquisition subsystem of a blood analyzer using a blood sample injecting valve. The acquisition subsystem can include a puncture needle 1, a pipeline 2 that connects the puncture needle 1 and a sample injecting valve 4 (which is located before the sample injecting valve 4), a photoelectric sensor 3 that is located before the sample injecting valve 4, the sample injecting valve 4, a quantitative pipeline 5 in the sample injecting valve 4, a photoelectric sensor 6 that is located after the sample injecting valve 4, a pipeline 7 of the sample injecting valve 4 that connects with an injector 8, and a sample tube 9. During sample acquisition, the puncture needle 1 may be inserted into the sample tube 9, and the blood sample inside the tube 9 can then be acquired into the pipeline 2, the pipeline 7 and the valve 4 using the injector 8. The entire acquisition process may be monitored by the photoelectric sensors 3 and 6.

There may be three kinds of substances in pipeline 2: dilute, air and blood sample. For the photoelectric sensor 3, the dilute can converge lights, and the transmittance of the dilute may be the highest; the transmittance of the air is about half of that for the dilute; and the transmittance of the blood is significantly lower than the dilute and the air, even the HGB (hemoglobin) content is lower than 30 g/L, the transmittance of the blood is about 20% lower than that of the dilute.

Figure 2:
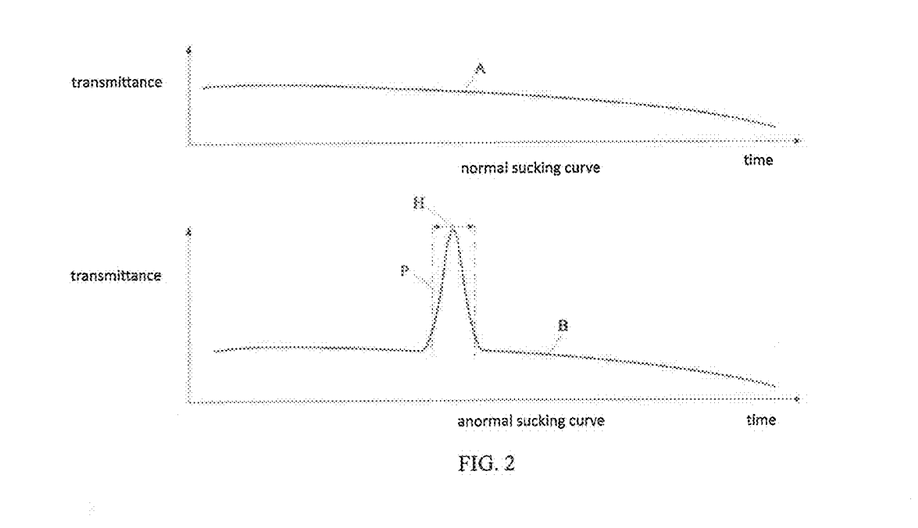
FIG. 2 shows a comparison of transmittance curves between normal acquisition process and anormal acquisition process.

Using the photoelectric sensor(s), the self-diagnosis methods and apparatuses described herein can monitor during sample acquisition changes in transmittance of the blood samples in the pipelines, so as to determine the characteristics of the blood samples flowing through the pipelines, and whether the samples in the quantitative pipeline of the injecting valve are uniform and uncontaminated (the measurement results can be anormal, if the blood samples in the quantitative pipeline are non-uniform or contaminated). FIG. 2 shows a comparison of transmittance curves between normal acquisition process and anormal acquisition process, where A represents the transmittance curve for normal acquisition, B represents the transmittance curve for anormal acquisition, P represents a pulse curve in the transmittance curve B, and H represents the width of the pulse curve. It can be seen that if a very small amount (on an order of 0.5 uL) of air or dilute is mixed into the blood sample when the sample enters into the injecting valve, such anomaly may be shown on the transmittance curve. The pulse curve P can be the detailed representation of such anomaly, and the width H of the pulse curve may indicate the severity of such anomaly. The wider the width H, the more anormal the acquisition process and the larger the measurement errors with respect to the real values.

Figure 3:
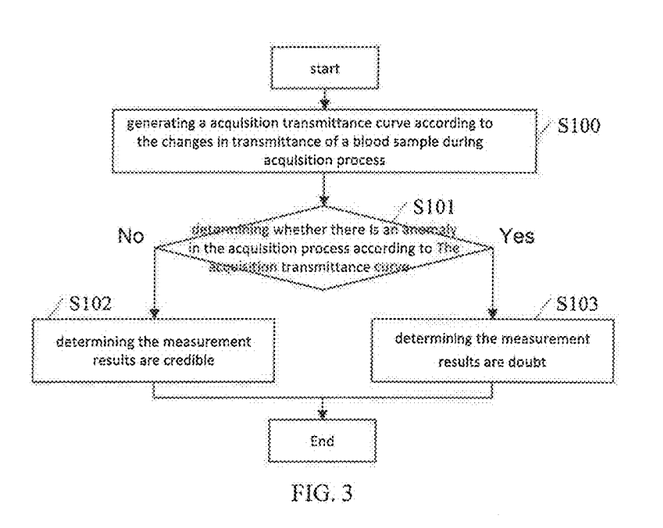
FIG. 3 shows a flow diagram of an example self-diagnosis method for measuring results from a blood analyzer according to an embodiment of the present disclosure.

FIG. 3 shows a flow diagram of an example self-diagnosis method for measuring results from a blood analyzer. This method can include:

Step S100: generating acquisition transmittance curve for a sample acquisition process according to changes in transmittance of blood samples during the acquisition process.

Step S101: determining whether there is an anomaly in the acquisition process according to the acquisition transmittance curve generated; if there is no anomaly in the acquisition process, then proceeding to step S102, otherwise, step S103.

Step S102: if there is no anomaly in the acquisition process, determining that the measurement results of the blood samples can be credible.

Step S103: if there is an anomaly in the acquisition process, determining that there may be doubt about the measurement results of the blood samples.

The above-described self-diagnosis method for measuring results from blood analyzers, by real-time monitoring of the change(s) in the acquisition transmittance curve during sample acquisition, can determine whether there is an anomaly in the acquisition process, thereby improving the accuracy of self-diagnosis and reducing the false positive rate.

Figure 4:
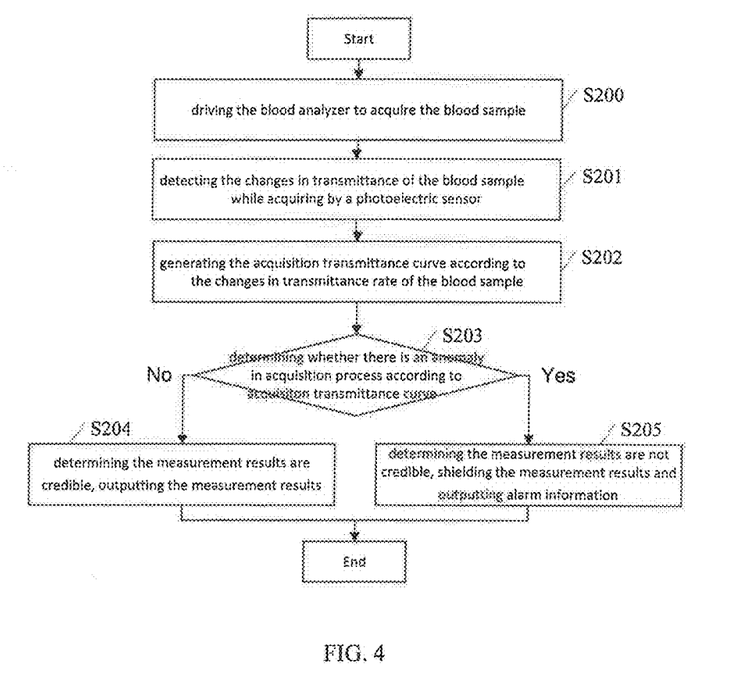
FIG. 4 also shows a flow diagram of an example self-diagnosis method for measuring results from a blood analyzer according to an embodiment of the present disclosure.

FIG. 4 also shows a flow diagram of an example self-diagnosis method for measuring results from a blood analyzer. In this example, the self-diagnosis of measurement results is described in more detail. This method can include:

Step S200: driving the blood analyzer to acquire a blood sample.

Step S201: detecting changes in transmittance of the blood sample during sample acquisition using a photoelectric detector. Specifically, acquisition transmittance of the blood sample flowing through the sampling pipelines of the blood analyzer can be monitored in real time, and the transmittance may then be converted to an electrical signal by the photoelectric detector.

Step S202: generating an acquisition transmittance curve according to the changes in transmittance of the blood sample during the sample acquisition process. Specifically, the electrical signal in step S201 is converted to a digital signal in this step, and the transmittance curve (see FIG. 2) is generated, with the acquisition time as the horizontal axis and the transmittance as the vertical axis. The transmittance curve generated can indicate the variation of the transmittance of the blood sample at different time during sample acquisition.

Step S203: determining whether there is an anomaly in the sample acquisition process according to the transmittance curve. If there is no anomaly during sample acquisition, then proceeding to S204; otherwise, step S205.

More specifically, if the transmittance curve is smooth, as curve A in FIG. 2, it can be determined that there is no anomaly in the sample acquisition process, and then proceed to S204; if there is a pulse in the transmittance curve, as curve B (including pulse curve P) in FIG. 2, it can be determined that there is an anomaly in the acquisition process, and then proceed to S205.

Furthermore, a user can set a threshold value H for the width of the pulse curve. If the width of the pulse curve in the transmittance curve exceeds the threshold value H, it can be determined that there is an anomaly in the sample acquisition process, and then proceed to S205; if the width of the pulse curve is equal to or less than the threshold value H, it can be determined that there is no anomaly in the acquisition process, and then proceed to S204. The sensitivity of the self-diagnostic results may be adjusted by setting the width threshold value H. The smaller the threshold value H, the more sensitive the self-diagnostic results; the larger the threshold value H, the less sensitive the self-diagnostic results. In some embodiments, the threshold value H can be between [4, 400] (unit, ms).

Step S204: if there is no anomaly in the sample acquisition process, it can be determined that the measurement results of the blood samples are credible, and the measurement results are output by the blood analyzer.

Step S205: if there is an anomaly in the sample acquisition process, it can be determined that the measurement results are not credible. The measurement results are shielded, and alarm information is outputted to warn the user that there is an anomaly in the measurement results which need to be measured again.

The above-described self-diagnosis method and apparatus for measuring results from blood analyzers, by real-time monitoring of the change(s) in the acquisition transmittance curve during sample acquisition, can determine whether there is an anomaly in the acquisition process, the anomaly measurement result is shield and warm the user, thereby improving the accuracy of self-diagnostic of measurement result, and reducing the false positive, at the same time, reducing workload and unnecessary re-measurement of users, and saving the measurement cost.

Figure 5:
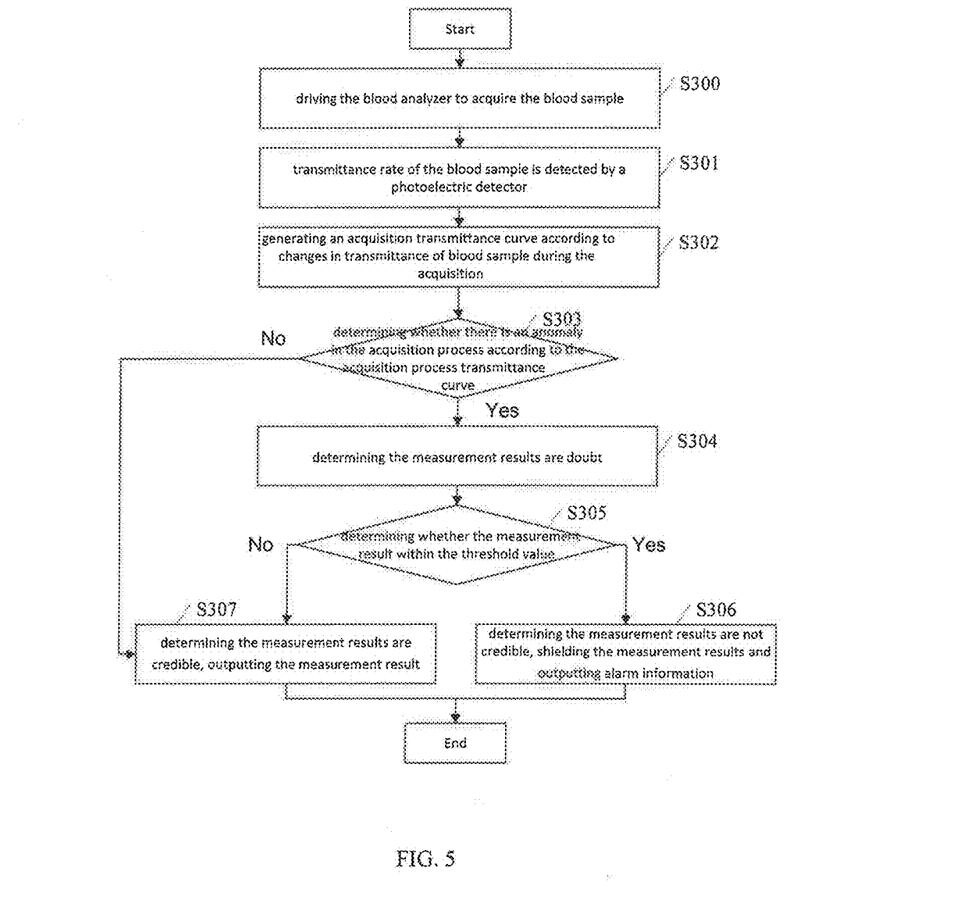
FIG. 5 further shows a flow diagram of an example self-diagnosis method for measuring results from a blood analyzer according to an embodiment of the present disclosure.

FIG. 5 shows a flow diagram of an example of self-diagnosis method for measuring results from a blood analyzer according to an embodiment of the present disclosure. In the present embodiment, real-time monitoring the transmittance curve, determining whether there is an anomaly in acquisition process, combining clinical statistics, and then improving the accuracy of self-diagnostic of measurement result.

In the present embodiment, how to combine clinical statistics to determine whether there is an anomaly in acquisition process, and how to combine the clinical statistics with the transmittance curve, will be described detailed in the flowing. Determining whether there is an anomaly in acquisition process by monitoring acquisition transmittance curve is the same as the above embodiment and will not be described here. Please refer FIG. 5, the self-diagnostic method comprising:

Step S300: driving the blood analyzer to acquire blood sample.

Step S301: optical transmittance of the blood sample is detected by a photoelectric detector.

Step S302: generating an acquisition transmittance curve according to changes in the optical transmittance of blood sample during the acquisition.

Step S303: determining whether there is an anomaly in the acquisition process according to the acquisition process transmittance curve; if there is no anomaly in the acquisition process, then proceeding to step S307, otherwise, step S304.

Step S304: if there is an anomaly in the acquisition process, the measurement results are doubt, and then proceeding to step S305, to determine whether the result is credible according to clinical statistics.

Step S305: acquiring the measurement results, and determine whether the results are within the threshold range, if the results are within the threshold range, then the results are not credible, and processed to step S306, if the results are outside the threshold range, then the results are credible, and processed to step S307.

Furthermore, the threshold range is setting by clinical statistics, the measurement result, including RBC (red blood cell), HGB (hemoglobin), and MCHC (Mean Corpuscular Hemoglobin Concentration) are considered, then combining with the normal reference range in clinical statistics to judge. For example, the normal reference range of RBC in clinical statistics is [3.5, 5.5], unit is 1012/L, the normal reference range of HGB in clinical statistics is [110, 160], unit is g/L, the normal reference range of MCHC in clinical statistics is [320, 340], unit is g/L.

In the present embodiment, assuming in measurement result of the blood sample, the threshold range are, HGB<120 g/L and MCHC<310 g/L or RBC<3×10$^{12}$/L and MCHC>400 g/L. If HGB<120 g/L and MCHC<310 g/L, the measurement results are not credible, or RBC<3×10$^{12}$/L and MCHC>400 g/L, the measurement results are not credible also, and processed to step S306. If the measurement results are outside the threshold range, the measurement results are credible, and processed to step S307. Because there are differences in clinical statistics between different people, there are also differences in traceability system between different libraries, the parameters may be adjusted by user, and then deviations are made, in order to make sure the result is accuracy, Kc is used to adjust the deviations, $$Kc = \frac{HGB \text{ calibration factor}}{RBC \text{ calibration factor} * MCV \text{ calibration factor}}$$

HGB Calibration factor is Calibration factor set for HGB (the default value is 1, the range between 0.75-1.25), RBC Calibration factor is calibration factor set for RBC (the default value is 1, the range between 0.75-1.25), MCV calibration factor is calibration factor set for MCV (the default value is 1, the range between 0.75-1.25).

In the present embodiment, in addition to threshold range of RBC, HGB, MCHC are set for reference, threshold range of other parameters may also be set for reference, for example, threshold range of WBC (White blood cell count), PLT (blood platelet), MCV (Mean Corpuscular Volume), etc are set for reference.

Step S306: shielding the measurement results which are not credible, and outputting alarm, for telling user that the measurement results are anormal and need re-measurement.

Figure 6:
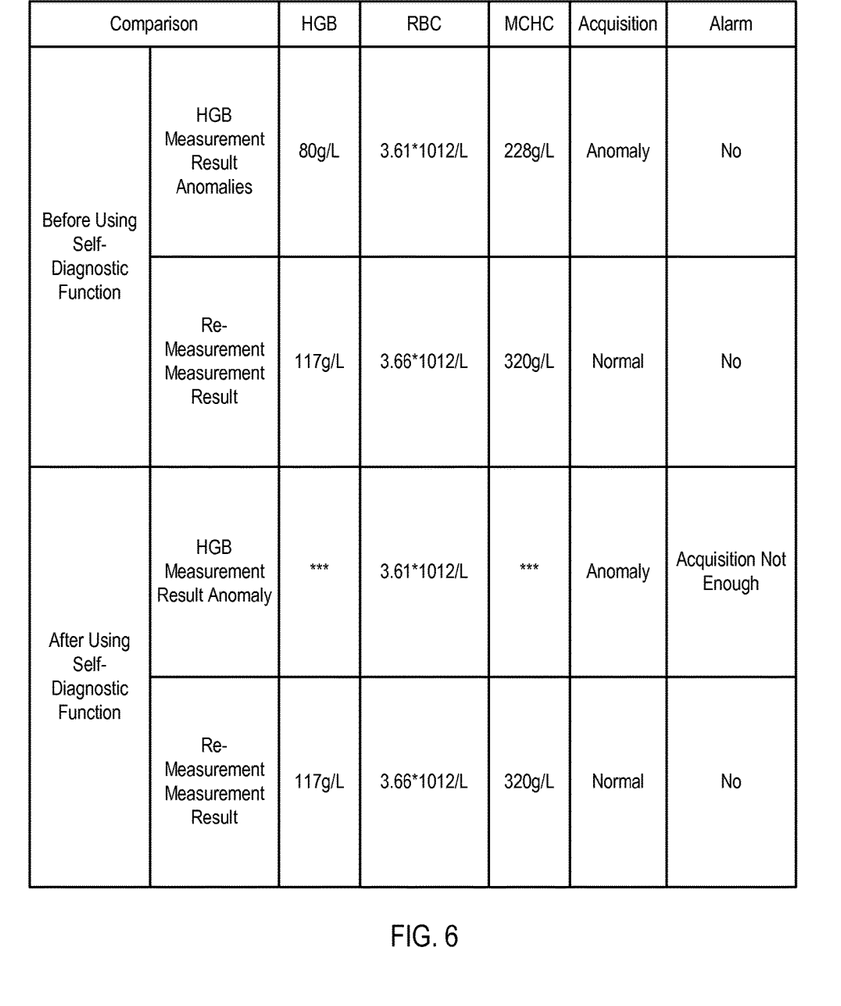
FIG. 6 shows a comparison of results before and after using a self-diagnostic method.

Step S307: the measurement results are deemed credible, outputting measurement results of blood sample directly. FIG. 6 shows a comparison of results of before and after using a self-diagnostic method. For the same blood sample, before using a self-diagnostic method, if the measurement result of HGB is lower than clinic normal levels, then anomaly is doubt, although there is alarm for the measurement results, there is no alarm for details, doctors will determine whether to re-measurement according to more information. After using the self-diagnostic method, if the measurement result is anormal, the result is shielded, and alarm for "sucking is not enough", then the doctors can determine to re-measurement, there is no more check work, and the doctors' work is not break.

The method of the present application could also be adjusted that, determining whether the measurement result is anormal firstly, then combining with acquisition transmittance curve of the blood samples, according to this to determine whether the measuring results are credible. That is, it is not necessary that S305 is after S303, as long as the blood analyzer finished measuring the blood sample, there are no strict sequences between S305 and S301-S303.

The present self-diagnostic method of measurement result of a blood analyzer, by monitoring the transmittance curve of the blood samples during sample acquisition, so as to determine whether the measurement results are anormal, at the same time, combine with the clinical statistics, further determine whether the measurement results are anormal, then the accuracy of measurement results are improved, and the false positive rate is reduced. The present application also could reduce the work of checking the measurement results, reducing the unnecessary re-measurement, and saving the cost of measurement.

Figure 7:
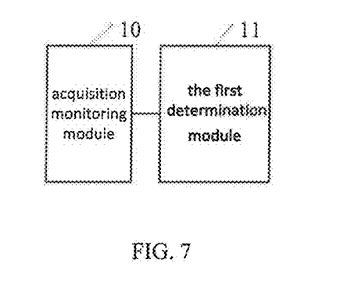
FIG. 7 shows a schematic diagram of an example self-diagnosis apparatus for measuring results from a blood analyzer according to an embodiment of the present disclosure.

FIG. 7 is a schematic diagram of an example self-diagnostic apparatus for measuring results from a blood analyzer. The apparatus comprise: acquisition monitoring module 10, for generating an acquisition transmittance curve according to changes in transmittance of a blood sample during an acquisition process; and determining whether there is an anomaly in the acquisition process according to acquisition transmittance curve.

The first determination module 11, for determining whether the measurement results of the blood sample are credible according to whether there is an anomaly in acquisition process; if there is no anomaly in the acquisition process, determining the measurement results are credible; if there is an anomaly in the acquisition process, determining that there is a doubt about the measurement results.

The self-diagnosis apparatus for measuring results from blood analyzers, by real-time monitoring of the acquisition transmittance curve during a sample acquisition process, can determining whether there is an anomaly in acquisition process according to the acquisition transmittance curve, so as to improve the accuracy of self-diagnostic of measurement result, reducing the false positive.

Figure 8:
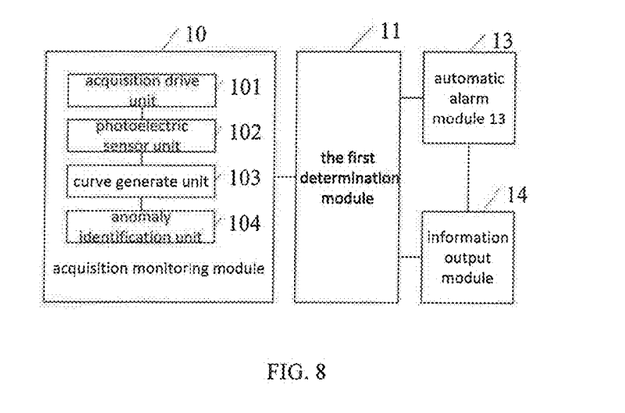
FIG. 8 also shows a schematic diagram of an example self-diagnosis apparatus for measuring results from a blood analyzer according to an embodiment of the present disclosure.

FIG. 8 shows a schematic diagram of an example of self-diagnosis apparatus for measuring results from a blood analyzer according to an embodiment of the present disclosure. The structure of the self-diagnostic apparatus will be described in detail in this embodiment. The apparatus including: acquisition monitoring module 10 and the first determination module 11.

Acquisition monitoring module 10, for generating an acquisition transmittance curve according to changes in transmittance of a blood sample during an acquisition process; determining whether there is an anomaly in acquisition process according to acquisition transmittance curve.

More specifically, acquisition monitoring module 10 include: acquisition drive unit 101, photoelectric sensor unit 102, curve generate unit 103 and anomaly identification unit 104.

Acquisition drive unit 101, for driving the blood analyzer to acquire the blood sample.

Photoelectric sensor unit 102, for detecting the changes of transmittance of the blood samples. More specifically, the photoelectric sensor real-time detecting transmittance of the blood samples which flow in acquisition tube, the transmittance is converted to an electrical signal by the photoelectric sensor.

Curve generating unit 103, for generating the acquisition transmittance curve according to changes in transmittance of the blood sample which is detected by the photoelectric sensor unit 102. More specifically, photoelectric sensor real-time detecting optical transmittance of the blood samples, and the optical transmittance is converted to an electrical signal, curve generate unit 103 will convert the analog to digital signal according to the electric signal, then the acquisition transmittance curve is generated, which the horizontal axis is acquisition sampling time, and the vertical axis is optical transmittance of the blood samples. This transmittance curve of the blood sample explains transmittance of the blood sample which flow in the acquisition tube at different time.

Anomaly identification unit 104, for determining whether there is an anomaly in the acquisition process according to the acquisition transmittance curve which is generated by curve generate unit 103. More specifically, if the transmittance curve is a smooth curve, for example, like curve A in FIG. 2, determining there is no anomaly in the acquisition process, if the transmittance curve, for example, like curve B in FIG. 2 (including pulse curve P), determining there is an anomaly in acquisition process.

Furthermore, a user can set a threshold H for the width of the pulse curve, if the width of the pulse curve in the transmittance curve exceeds width threshold H, abnormal identification unit 104 determining abnormal is happened while acquisition, when the width of the pulse curve dose exceeds width threshold H, anomaly identification unit 104 determining there is an anomaly in the sample acquisition. The sensitivity of the measurement result self-diagnosis of the blood analyzer is adjusted by setting the width threshold H, the smaller the width threshold H, the more sensitive the self-diagnostic result, the larger the threshold H, the less sensitive the self-diagnostic. In practical applications, threshold H can be between [4, 400] (unit: millisecond).

The first determination module 11, for determining whether the measurement result of the blood sample are credible according to whether there is anomaly in the acquisition process which is detected by acquisition monitoring module 10, if there is no anomaly in the acquisition process, determining that the measured results are credible; if there is an anomaly in the acquisition process, determining that there is a doubt about the measurement results.

Furthermore, the present embodiment of self-diagnostic apparatus of the blood analyzer measurement results, further comprising:

Automatic alarm module 13, for when the measurement result is doubt which is determined by the first determination module 11, alarm information is output by information output module 14. The alarm information warns the user that there is an anomaly in this measurement, and the blood sample needs re-measurement.

Information output module 14, for when the measurement results are credible which is determined by the first determination module 11, outputting measurement results of the blood sample; when the measurement results are doubt, shielding the measurement results and outputting alarm information by automatic alarm module 13.

The present self-diagnostic apparatus of measurement result of a blood analyzer, by monitoring the acquisition transmittance curve during sucking sample acquisition process, can determine whether there is an anomaly in the acquisition process, anormal result is shielded and warn the user, then the accuracy of measurement results are improved, and the false positive rate is reduced. The present application also could reduce the work of checking the measurement results, reducing the unnecessary re-measurement, and saving the cost of measurement.

Figure 9:
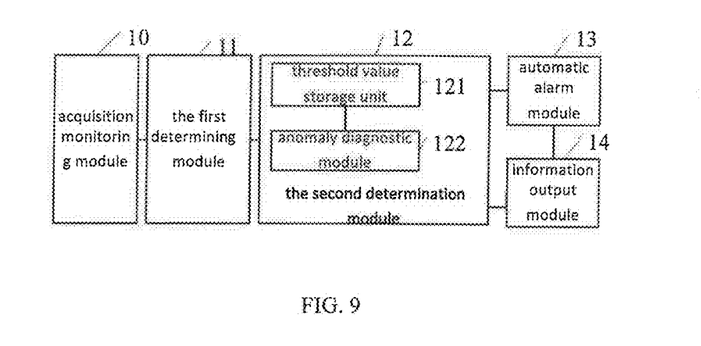
FIG. 9 further shows a schematic diagram of an example self-diagnosis apparatus for measuring results from a blood analyzer according to an embodiment of the present disclosure.
Figure 10:
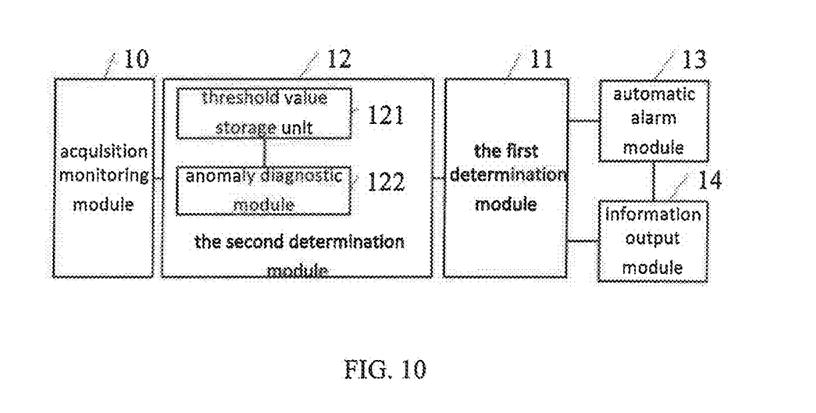
FIG. 10 shows another schematic diagram of the example self-diagnosis apparatus shown in FIG. 9.

FIG. 9 is a schematic diagram of an example self-diagnostic apparatus for measuring result from a blood analyzer. The difference is adding a second determination module, and the second determination module could determine whether there is an anomaly in measurement result based on clinical statistics. The second determination module combine with the first determination module, the accuracy of self-diagnosis to the results are improved further.

Please refer to FIG. 9, the present embodiment provides a self-diagnostic apparatus of a blood analyzer measurement result, comprising:

Acquisition monitoring module 10, for generating the acquisition transmittance curve according to changes in transmittance of the blood samples during an acquisition process, and determining whether there is an anomaly in the acquisition process according to the acquisition transmittance curve.

The first determination module 11, for determining whether the measurement results of the blood sample are credible according to whether there is an anomaly in the acquisition process; if there is no anomaly in the acquisition process, determining that the measured results are credible; if there is an anomaly in the acquisition process, determining that there is a doubt about the measurement results.

The second determination 12, for determining whether the measurement results are within the threshold range, if the measurement results are within the threshold range, determining the measurement results are not credible; if the measurement results are outside the measurement result, determining the measurement result are credible. More specifically, the second determination module 12 comprising:

A threshold value storage unit 121, for storing a threshold range, which is based on clinical statistics, the threshold range is used for determining whether the measurement results are credible. The preset threshold range of the threshold value storage unit 121 is set according to clinical statistics, the value range mainly refer to the measurement result of RBC, HGB and MCHC, determining according to the normal reference range of RBC, HGB, and MCHC in clinical statistics. The normal reference range of RBC in clinical statistics is [3.5, 5.5], unit is 1012/L, the normal reference range of HGB in clinical statistics is [110, 160], unit is g/L, the normal reference range of MCHC in clinical statistics is [320, 340], unit is g/L.

In the present embodiment, in addition to threshold range of RBC, HGB, MCHC are set for reference, threshold range of other parameters may also be set for reference, for example, threshold range of WBC, PLT, MCV, etc are set for reference.

Anomaly diagnostic module 122, for determining whether the measurement results of the blood sample are outside the preset threshold range of the threshold value storage unit 121, if the measurement results are within the threshold range, determining the measurement results are not credible; if the measurements are outside the measurement results, determining the measurement results are credible.

More specifically, in the present embodiment, the threshold value range which is preset in the threshold value storage unit 121 are, HGB<120 g/L and MCHC<310 g/L or RBC<3×10$^{12}$/L and MCHC>400 g/L. If HGB<120 g/L and MCHC<310 g/L, the anomaly diagnostic module 122 determining the measurement results are not credible, or RBC<3×10$^{12}$/L and MCHC>400 g/L, the anomaly diagnostic module 122 determining the measurement results are not credible also. If the measurement results are not within the threshold value range, the anomaly diagnostic module 122 determining the measurement results are credible. Because there are differences in clinical statistics between different people, there are also differences in traceability system between different libraries, the parameters may be adjusted by user, and then deviations are made, in order to make sure the result is accuracy, Kc is used to adjust the deviation.

$$Kc = \frac{HGB \text{ calibration factor}}{RBC \text{ calibration factor} * MCV \text{ calibration factor}}$$

HGB Calibration factor is Calibration factor set for HGB (the default value is 1, the range between 0.75-1.25), RBC Calibration factor is Calibration factor set for RBC (the default value is 1, the range between 0.75-1.25), MCV Calibration factor is Calibration factor set for MCV (the default value is 1, the range between 0.75-1.25).

Automatic alarm module 13, for when the measurement results are determined not credible by the second determination module 12, outputting alarm information by the information output module 14. The alarm information warns the user that there is anomaly in this measurement, and the blood sample needs re-measurement.

Information output module 14, for when the measurement results are determined credible by the first determination module 11 and/or the second determination module 12, outputting the measurement results directly. When the measurement result is determined not credible by the second determination module 12, shielding the measurement result of the blood sample and outputting alarm information by automatic alarm module 13. Please refer to FIG. 6, is comparison of result before and after using a self-diagnosis apparatus, for the same blood sample, before using the self-diagnosis apparatus, HGB is lower than normal clinical level, anomaly is suspected, although there is alarm for the measurement result, there is no alarm for details, doctors will determine whether to re-measurement according to more information. When using the present self-diagnosis apparatus to measurement result, if there is an anomaly at the first measurement, the result will be shielded, apparatus will warn "acquisition is not enough", then doctors will re-measurement if see this warn, without additional examination and confirm the work, so normal work flow will not be disturbed.

The method of the present application could also be adjusted that, determining whether there is an anomaly in the measurement result firstly by the second determination module 12, then determining whether the measurement result is anormal combining with acquisition transmittance curve of the blood samples by the first determination module 11, the accuracy of self-diagnosis to the results will be improved, and the false positive rate will be decreased. The present application could also release the pressure to check the result, reducing unnecessary re-measurement, and saving the cost of measurement.

The flow of the self-diagnosis method can be realized by computer or related hardware, all procedures may be stored in a computer readable storage medium, when the program could be executed as the present method. Storage media could be disk, CD, Read-Only Memory (ROM) or Random Access Memory (RAM), etc.

Those having skill in the art will appreciate that many changes may be made to the details of the above-described embodiments without departing from the underlying principles of the invention. The scope of the present invention should, therefore, be determined only by the following claims.

What is claimed is:
1. A method for self-diagnosis of measurement results of a blood sample from a blood analyzer comprising an acquisition driver and a pipeline, the method comprising:
flowing the blood sample from a sample tube through the pipeline to the acquisition driver for a sample acquisition;
detecting changes with time in an optical transmittance of the blood sample in the pipeline by using a photoelectric sensor during the sample acquisition;

generating an acquisition transmittance curve according to the changes versus time in the optical transmittance of the blood sample; and determining whether there is an anomaly in the acquisition process according to the acquisition transmittance curve.

2. The method of claim 1, further comprising: determining whether the measurement results are within a threshold range; if the measurement results are within the threshold range, determining that the measurement results are not credible; if the measurement results are outside-the threshold range, determining that the measurement results are credible.

3. The method of claim 2, wherein the threshold range is set by clinical statistics.

4. The method of claim 3, wherein the threshold range is: HGB (hemoglobin)<120 g/L and MCHC (Mean Corpuscular Hemoglobin Concentration)<310 g/L; or RBC (red blood cell)<3×1012/L and MCHC>400 g/L; or HGB<120 g/L and MCHC<Kc*310 g/L; or RBC<3×1012/L and MCHC>Kc*400 g/L;

$$Kc = \frac{HGB \text{ calibration factor}}{RBC \text{ calibration factor} * MCV \text{ calibration factor}}$$

if the measurement results are within the threshold range, determining that the measurement results are not credible; otherwise, determining that the measurement results are credible, wherein MCV stands for Mean Corpuscular Volume.

5. The method of claim 2, further comprising: outputting the measurement results if the measurement results are determined to be credible; shielding the measurement results if the measurement results are determined to be not credible, and outputting alarm information.

6. The method of claim 1, wherein determining whether there is an anomaly in the acquisition process acquisition comprises:

if the acquisition transmittance curve is smooth, determining that there is no anomaly in the acquisition process; if there is a pulse in the acquisition transmittance curve, determining that there is an anomaly in the acquisition process.

7. An apparatus with self-diagnosis of measurement results of a blood sample, the apparatus comprising:

an acquisition driver for a sample acquisition;

an acquisition monitoring module comprising a photoelectric sensor unit for detecting changes with time in an optical transmittance of the blood sample in a pipeline coupled between a sample tube and the acquisition driver, for generating an acquisition transmittance curve according to the changes versus time in an optical transmittance of the blood sample during an acquisition process, and determining whether there is an anomaly in the acquisition process according to the acquisition transmittance curve; and a first determination module coupled to the acquisition monitoring module, for determining whether the measurement results of the blood sample are credible according to whether there is an anomaly in the acquisition process; if there is no anomaly in the acquisition process, determining that the measurement results are credible; if there is an anomaly in the acquisition process, determining that there is a doubt about the measurement results.

8. The apparatus of claim 7, further comprising:

a second determination module coupled to the first determination module, for determining whether the measurement results are within a threshold range;

if the measurement results are within the threshold range, determining that the measurement results are not credible; if the measurement results are outside the threshold range, determining that the measurement results are credible.

9. The apparatus of claim 8, wherein the second determination module comprises:

a threshold value storage unit, for storing a threshold range, which is based on clinical statistics, the threshold range is used for determining whether the measurement results are credible; and an anomaly diagnostic module coupled to the threshold value storage unit, for determining whether the measurement results of the blood sample are within the threshold range; if the measurement results are within the threshold range, determining that the measurement results are not credible; if the measurement results are outside the threshold range, determining that the measurement results are credible.

10. The apparatus of claim 8, further comprising:

an automatic alarm module coupled to the first and/or second determination module, for outputting alarm information when the measurement results are determined to be not credible by the second determination module; and an information output module coupled to the automatic alarm module, for outputting the measurement results when the measurement results are determined to be credible by the first determination module and/or the second determination module; shielding the measurement results when the measurement results are determined to be not credible by the second determination module.

11. The apparatus of claim 7, wherein the acquisition monitoring module further comprises:

an acquisition driving unit coupled to the photoelectric sensor unit, for driving the blood analyzer to acquire the blood sample;

a curve generating unit coupled to the photoelectric sensor unit, for generating the acquisition transmittance curve according to the changes in the optical transmittance rate of the blood sample versus time; and an anomaly identification unit coupled to the curve generating unit, for determining whether there is an anomaly in the acquisition process according to the acquisition transmittance curve.

12. The apparatus of claim 11, wherein the anomaly identification unit determines that there is no anomaly in the acquisition process when the acquisition transmittance curve is smooth, and determines that there is an anomaly in the acquisition process when there is a pulse in the acquisition transmittance curve.

\* \* \* \* \*